United States Patent [19]

Sathe

[11] 4,176,138
[45] Nov. 27, 1979

[54] PROCESS FOR PREPARING P-AMINOPHENOL IN THE PRESENCE OF DIMETHYLDODECYLAMINE SULFATE

[75] Inventor: Sharad S. Sathe, Maryland Heights, Mo.

[73] Assignee: Mallinckrodt, Inc., St. Louis, Mo.

[21] Appl. No.: 955,442

[22] Filed: Oct. 27, 1978

[51] Int. Cl.$^2$ ............................................. C07C 89/00
[52] U.S. Cl. ................................................. 260/575
[58] Field of Search ............................... 260/575, 580

[56] References Cited

U.S. PATENT DOCUMENTS

| | | | |
|---|---|---|---|
| 2,198,249 | 4/1940 | Henke et al. | 260/575 |
| 2,765,342 | 10/1956 | Spiegler | 260/575 |
| 3,383,416 | 5/1968 | Benner | 260/575 |
| 3,535,382 | 10/1970 | Brown et al. | 260/575 |
| 3,654,365 | 4/1972 | Daunis et al. | 260/575 |

FOREIGN PATENT DOCUMENTS 856366 12/1960 United Kingdom .................... 260/575

OTHER PUBLICATIONS

Bamberger, "Deutsche Chemische Gesellschaft Berichte", 27, pp. 1347-1350 (1894).
Bamberger, "Deutsche Chemische Gesellschaft Berichte", 27, pp. 1548-1557 (1894).

*Primary Examiner*—Winston A. Douglas
*Assistant Examiner*—John Doll
*Attorney, Agent, or Firm*—Roy J. Klostermann

[57] ABSTRACT

The preparation of p-aminophenol by the catalytic hydrogenation of nitrobenzene in an acid reaction medium containing an aqueous isopropyl alcohol solution of trimethyldodecylammonium chloride leads to the formation of chloro- and isopropoxyaniline impurities. These end up in the by-product aniline. The substitution of dimethyldodecylamine sulfate for the quaternary salt eliminates these impurities without significant adverse effect on the yield, production rate or purity of the p-aminophenol.

6 Claims, No Drawings

PROCESS FOR PREPARING P-AMINOPHENOL IN THE PRESENCE OF DIMETHYLDODECYLAMINE SULFATE

BACKGROUND OF THE INVENTION

This invention relates to the field of organic chemistry, and more particularly, to an improvement in the process for the preparation of p-aminophenol from nitrobenzene.

p-Aminophenol (PAP) is an important chemical intermediate used in the preparation of the analgesic, acetaminophen. A number of other derivatives having a wide variety of industrial applications may also be prepared from PAP. One method for preparing PAP involves the catalytic hydrogenation of nitrobenzene in an acid medium. In this process, phenylhydroxylamine is first formed, and this intermediate promptly rearranges in the acid reaction medium to form PAP. This rearrangement of phenylhydroxylamine in acid solution was first described in two 1894 reports by Bamberger (Ber. 27, 1347 and 1548). While the desired reaction proceeds as indicated, a competing second reation takes place to a varying extent, resulting in the production of aniline, rather than PAP. Lesser amounts of other by-products are also formed.

Henke, et al. (U.S. Pat. No. 2,198,249) were the first to disclose a process for the preparation of PAP by the catalytic hydrogenation of nitrobenzene in an acid medium.

A number of improvements have since been reported. For example, Spiegler (U.S. Pat. No. 2,765,342) studied the reaction extensively. Among the factors explored by Spiegler was the effect on reduction rate and p-aminophenol yield of including a surfactant selected from among several quaternary ammonium compounds and several non-quaternary compounds. Among the quaternary ammonium compounds used was dodecyl trimethylammonium chloride; the non-quaternary compounds investigated included two simple tertiary amine salts: triethylamine sulfate and tributylamine sulfate, as well as dioctadecyl propyleneamine dioleate. From a plot of rate and yield data, Spiegler concluded that the rate/yield performance of all of the quaternary ammonium compounds examined was superior to that of the non-quaternary compounds.

Later, Brown et al. (U.S. Pat. No. 3,535,382) reported that certain nonionic polyether polyol surfactants could be substituted for Spiegler's quaternary ammonium compounds.

R. G. Benner (U.S. Pat. No. 3,383,416) used the Henke et al. approach of charging all the nitrobenzene at once, but used a carbon-supported platinum catalyst and quaternary ammonium surfactant, preferably dodecyl trimethylammonium chloride, as disclosed by Spiegler. Benner purposely interrupted the hydrogenation well before all the nitrobenzene had been consumed. In the presence of two liquid phases, aqueous and nitrobenzene, a carbon-supported platinum catalyst is preferentially wetted by the nitrobenzene, so most of the catalyst is suspended in the nitrobenzene phase. Thus, when hydrogenation is interrupted while there is still a distinct nitrobenzene phase, the catalyst preferentially remains suspended in the lower nitrobenzene layer, permitting the removal of the upper aqueous solution of PAP and aniline by decantation. The PAP is then recovered from the aqueous layer and purified.

One method of recovering the PAP involves neutralizing the aqueous phase to precipitate the PAP. At the same time, the aniline, which is dissolved as its salt in the acid solution, separates as an organic phase in the neutral solution and is readily separated from the aqueous phase.

Although PAP is the principal product of the process discussed above, the by-product aniline is also of commercial significance. While the relative yields of PAP and aniline are sensitive to a number of variables, such as hydrogen pressure, acidity, catalyst, temperature, surfactant, degree of agitation, etc., the by-product aniline yield will often amount to 10 to 25% or more of the yield of PAP. Thus, the marketability of the by-product aniline is a significant factor in the overall economy of the PAP process.

It has been found that one drawback to the use of trimethyldodecylammonium chloride as a surfactant in the PAP-from-nitrobenzene process is that it leads to undesirable minor by-products in the aniline phase. First of all, the chloride introduced in the quaternary ammonium salt leads to the formation of small amounts of o and p-chloroaniline, respectively. Morever, the form in which the quaternary ammonium salt is supplied commercially is a solution in water/isopropyl alcohol. The isopropyl alcohol thus introduced into the process with the quaternary salt leads to the formation of small amounts of o and p-isopropoxyaniline, respectively. These chloro- and isopropoxyaniline impurities follow the aniline in the separation steps and collectively appear to the extent of about 1% in the crude aniline thus recovered. Since by-product aniline containing these impurities must compete in the market place with aniline from other sources which does not contain these impurities, their presence in the aniline is a drawback.

Accordingly, the use in the PAP-from-nitrobenzene process of a process additive which possesses the useful characteristics of trimethyldodecylammonium chloride, but which avoids the production of chloro- and isopropoxyanilines would be desirable. It is an object of this invention to define such an additive. Other objects will be in part apparent and in part pointed out hereinafter.

SUMMARY OF THE INVENTION

Briefly, the present invention is directed to an improved process for preparing p-aminophenol, with aniline as a by-product, by the catalytic hydrogenation of nitrobenzene in an acidic reaction medium containing dimethyldodecylamine sulfate.

When dimethyldodecylamine sulfate is substituted for trimethyldodecylammonium chloride in a standardized PAP-from-nitrobenzene process, the resulting by-product aniline is free of chloro- and isopropoxyaniline impurities, yet no significant adverse effects on yield, production rate or purity of the PAP are observed.

As pointed out earlier, the catalytic hydrogenation of nitrobenzene to produce PAP is carried out in an acidic reaction medium. In this process, the preferred acidifying agent is sulfuric acid, although other acids have been used. The addition of dimethyldodecylamine to the reaction medium may be accomplished either by adding the free amine to the acid reaction medium or by previously dissolving the amine in dilute sulfuric acid and adding that solution to the reaction vessel.

While the dimethyldodecylamine might be added in the form of a non-halide salt other than the sulfate by dissolving the free amine in a non-hydrohalic acid other than sulfuric acid, there is no advantage and there are potential disadvantages to adding diverse anions to the reaction mixture.

The minimum proportion of the additive that should be employed in the process is about 0.01% of dimethyldodecylamine by volume, based on the aqueous reaction medium. Ordinarily no advantage is obtained by using more than about 0.2%. The preferred range is about 0.05 to about 0.15%.

the following examples illustrate the invention.

EXAMPLES

Three hydrogenations of nitrobenzene were carried out as described below.

A mixture of distilled water, surfactant and 3% Pt/C catalyst (250 mg) in a 2 liter reaction vessel equipped for pressure hydrogenation, was flushed with nitrogen, then heated to 70° C. under hydrogen. With vigorous agitation, sulfuric acid (80 g. of 95–98% reagent grade/Sp.Gr. 1.84) was added during a period of 2–3 minutes, the temperature rising to about 85° C. Nitrobenzene (108 g.) was added rapidly, and hydrogenation was carried out under temperature and pressure control for several hours. The hydrogenation was interrupted, and the aqueous and nitrobenzene phases were separated, the catalyst remaining suspended in the nitrobenzene phase. Variable data applicable to the three runs are set forth in Table 1.

Table 1

| | Example 1 | Example 2 | Standard Run |
|---|---|---|---|
| Water (ml) | 640 | 650 | 650 |
| Surfactant | Dimethyldodecylamine sulfate(a) | Dimethyldodecylamine sulfate(b) | Trimethyldodecylammonium chloride(c) |
| Reaction temperature/°C. | 84–88 | 85–88 | 83–88 |
| Hydrogen pressure (inches of water) | 6–25 | 7–25 | 7–22 |
| Reaction time (hours) | 7 | 5 | 7 |

(a)1.0 ml. of dimethyldodecylamine in 10 ml. of 10% H$_2$SO$_4$
(b)0.5 ml. of dimethyldodecylamine in 10 ml. of 10% H$_2$SO$_4$
(c)2.0 ml. of 33% solution of quaternary salt in water/isopropyl alcohol.

The reaction mixtures were stored under nitrogen (Ex. 1: overnight; Ex. 2 and standard: over weekend). A 5 ml portion of the aqueous phase of each was then removed and diluted to 50 ml with 10% H$_2$SO$_4$ for PAP and aniline assays.

The following operations were then carried out on each run. The catalyst was filtered from the remainder of the reaction mixture and the organic and aqueous phases were separated. The aqueous phase was extracted with toluene (2×100 ml) to remove most of the residual dissolved nitrobenzene. The aqueous phase was then cooled, with stirring, to 4° C. and was then neutralized (pH 7–8) with ammonium hydroxide solution and stirred (5–10° C.) for an hour to precipitate PAP.

The precipitated PAP was filtered off, washed once with distilled water (50 ml.) and twice with reagent aniline (1×75 ml and 1×25 ml), and twice with toluene (2×100 ml), then air dried.

The filtrate from the PAP filtration was allowed to stand 15 minutes, during which time a separate aniline phase formed and was separated from the aqueous phase.

Pertinent data on the three runs are shown in Table 2.

Table 2

PRODUCT CONCENTRATION IN AQUEOUS PHASE OF REACTION MIXTURE

| | PAP (mg/ml) | Aniline (mg/ml) | Ratio PAP/aniline | Isolated PAP(g)* |
|---|---|---|---|---|
| Ex. 1 | 47.7 | 9.7 | 4.9 | 27.7 |
| Ex. 2 | 32.1 | 5.9 | 5.4 | 18.1 |
| Standard Run | 38.1 | 7.5 | 5.1 | 22.1 |

*Precipitated, washed, air dried.

The by-product aniline obtained in the Standard Run contained a combined total of about 1% of o- and p-chloroaniline and o- and p-isopropoxyaniline. The aniline from Examples 1 and 2 was essentially free of these impurities.

In view of the above, it will be seen that the objects of the invention are achieved and other advantageous results obtained.

As various changes could be made in the above methods without departing from the scope of the invention, it is intended that all matter contained in the above description shall be interpreted as illustrative and not in a limiting sense.

What is claimed:

1. A method for preparing p-aminophenol, with aniline as a by-product, by the catalytic hydrogenation of nitrobenzene in an acidic reaction medium containing dimethyldodecylamine sulfate.

2. A method as defined by claim 1 wherein the catalyst comprises platinum supported on carbon.

3. A method as defined by claim 1 wherein the reaction medium is acidified with sulfuric acid.

4. a method as defined by claim 3 wherein about 0.01% to about 0.2% by volume of dimethyldodecylamine, based on the aqueous medium, is used.

5. A method as defined by claim 4, wherein the proportion of dimethyldodecylamine is about 0.05% to about 0.15%.

6. In a method for preparing p-aminophenol, with aniline as a by-product, by the catalytic hydrogenation of nitrobenzene in an acidic reaction medium containing a surfactant, the improvement which comprises using dimethyldodecylamine sulfate as the surfactant.

* * * * *